(12) United States Patent
Roisin et al.

(10) Patent No.: US 9,480,569 B2
(45) Date of Patent: Nov. 1, 2016

(54) PROSTHETIC TIBIAL BASE, AND PROSTHETIC TIBIAL INSERT INTENDED TO BE IMMOBILIZED ON SUCH A PROSTHETIC TIBIAL BASE

(71) Applicant: ANATOMIC, Marseilles (FR)

(72) Inventors: Alain Roisin, Marnes la Coquette (FR); William Van Hille, Veyre Monton (FR); Michel Yvroud, Coin les Cuvry (FR); Etienne Peronne, Chamaliers (FR); Philippe Piriou, Belloy en Frane (FR); Olivier Guingand, Paris (FR); Frederic Borrione, Marseilles (FR); Vincent Oget, Reims (FR); Jean-Pierre Piton, Sanry les Vigy (FR); Luc Lhotellier, Paris (FR); Olivier Guyen, Lyons (FR); François Bonnomet, Oberhausbergen (FR); Jean-François Potel, Toulouse (FR); Michel Boussaton, Roques sur Garonne (FR)

(73) Assignee: ANATOMIC, Marseille (FR)

( * ) Notice: Subject to any disclaimer, the term of this patent is extended or adjusted under 35 U.S.C. 154(b) by 0 days.

(21) Appl. No.: 14/423,507

(22) PCT Filed: Jul. 25, 2013

(86) PCT No.: PCT/FR2013/051792
§ 371 (c)(1),
(2) Date: Feb. 24, 2015

(87) PCT Pub. No.: WO2014/029928
PCT Pub. Date: Feb. 27, 2014

(65) Prior Publication Data
US 2015/0202048 A1    Jul. 23, 2015

(51) Int. Cl.
*A61F 2/38*     (2006.01)
*A61F 2/30*     (2006.01)

(52) U.S. Cl.
CPC .......... *A61F 2/389* (2013.01); *A61F 2002/305* (2013.01); *A61F 2002/30164* (2013.01);

(Continued)

(58) Field of Classification Search
CPC ........ A61F 2/38; A61F 2/389; A61F 2/3868; A61F 2002/30164; A61F 2002/30172; A61F 2002/30181
USPC ......... 623/20.14, 20.15, 20.18, 20.27, 20.32, 623/20.28, 20.26
See application file for complete search history.

(56) References Cited

U.S. PATENT DOCUMENTS

| 5,413,604 | A | * | 5/1995 | Hodge .................. A61F 2/3868 623/20.28 |
| 5,871,546 | A | * | 2/1999 | Colleran .................. A61F 2/38 623/20.28 |

(Continued)

FOREIGN PATENT DOCUMENTS

| EP | 2 042 131 A2 | 4/2009 |
| EP | 2 042 134 A1 | 4/2009 |

(Continued)

OTHER PUBLICATIONS

Oct. 10, 2013 International Search Report issued in International Application No. PCT/FR2013/051792.

*Primary Examiner* — Alvin Stewart
(74) *Attorney, Agent, or Firm* — Oliff PLC (57) ABSTRACT

The invention relates to a base that includes a unit for osseous attachment onto a tibia, and a plate having posterior, anterior, medial and lateral edges; a posterior pin and an anterior pin having a posterior flat section and an anterior flat section; two posterior lugs protruding above the plate and arranged on the posterior edge of each side of the posterior pin; and two anterior lugs arranged on each side of the anterior pin. The posterior flat section and the anterior flat section are arranged so as to simultaneously engage with the insert. Each posterior tab includes a support extension for inserting, in an anteroposterior direction, a complementary support tab of the insert. Each anterior lug includes a unit for snap-coupling the insert onto the base.

16 Claims, 4 Drawing Sheets

(52) U.S. Cl.
CPC ............... *A61F2002/30329* (2013.01); *A61F 2002/30604* (2013.01); *A61F 2002/30616* (2013.01); *A61F 2002/30878* (2013.01); *A61F 2002/30884* (2013.01)

(56) References Cited

U.S. PATENT DOCUMENTS

| | | | | |
|---|---|---|---|---|
| 6,299,646 B1* | 10/2001 | Chambat | ............... | A61F 2/3868 623/20.33 |
| 6,361,564 B1* | 3/2002 | Marceaux | ............... | A61F 2/3868 623/20.28 |
| 6,379,388 B1* | 4/2002 | Ensign | ............... | A61F 2/389 623/20.21 |
| 6,500,208 B1* | 12/2002 | Metzger | ............... | A61F 2/389 623/20.15 |
| 6,506,215 B1* | 1/2003 | Letot | ............... | A61F 2/3868 623/20.14 |
| 6,569,202 B2* | 5/2003 | Whiteside | ............... | A61F 2/389 623/20.28 |
| 6,623,526 B1* | 9/2003 | Lloyd | ............... | A61F 2/3868 623/20.28 |
| 6,986,791 B1* | 1/2006 | Metzger | ............... | A61F 2/3868 623/20.24 |
| 7,947,082 B2* | 5/2011 | Guidera | ............... | A61F 2/3868 623/20.28 |
| 8,128,703 B2* | 3/2012 | Hazebrouck | ............... | A61F 2/38 623/20.14 |
| 8,403,993 B2* | 3/2013 | Aram | ............... | A61F 2/3868 623/20.28 |
| 8,470,047 B2* | 6/2013 | Hazebrouck | ............... | A61F 2/389 623/20.31 |
| 8,591,594 B2* | 11/2013 | Parisi | ............... | A61F 2/3886 623/20.21 |
| 8,603,101 B2* | 12/2013 | Claypool | ............... | A61F 2/389 606/102 |
| 8,702,803 B2* | 4/2014 | Otto | ............... | A61F 2/389 623/20.28 |
| 8,764,840 B2* | 7/2014 | Sanford | ............... | A61F 2/389 623/20.28 |
| 8,858,643 B2* | 10/2014 | Parisi | ............... | A61F 2/3886 623/20.28 |
| 8,894,715 B2* | 11/2014 | Metzger | ............... | A61F 2/3868 623/20.15 |
| 8,968,412 B2* | 3/2015 | Wogoman | ............... | A61F 2/4684 623/20.15 |
| 9,011,547 B2* | 4/2015 | Auger | ............... | A61F 2/3868 623/20.19 |
| 9,204,967 B2* | 12/2015 | Wyss | ............... | A61F 2/38 |
| 2002/0055784 A1* | 5/2002 | Burstein | ............... | A61F 2/389 623/20.28 |
| 2003/0014122 A1* | 1/2003 | Whiteside | ............... | A61F 2/389 623/20.32 |
| 2003/0153979 A1* | 8/2003 | Hughes | ............... | A61F 2/30767 623/20.28 |
| 2004/0102852 A1* | 5/2004 | Johnson | ............... | A61F 2/38 623/20.15 |
| 2004/0243244 A1* | 12/2004 | Otto | ............... | A61F 2/3836 623/20.27 |
| 2005/0143832 A1* | 6/2005 | Carson | ............... | A61F 2/3886 623/20.28 |
| 2005/0209702 A1* | 9/2005 | Todd | ............... | A61F 2/3868 623/20.33 |
| 2006/0052875 A1* | 3/2006 | Bernero | ............... | A61F 2/38 623/20.33 |
| 2006/0224244 A1* | 10/2006 | Thomas | ............... | A61L 27/56 623/20.28 |
| 2007/0203582 A1* | 8/2007 | Campbell | ............... | A61F 2/389 623/20.34 |
| 2008/0051908 A1* | 2/2008 | Angibaud | ............... | A61F 2/389 623/20.32 |
| 2009/0082873 A1* | 3/2009 | Hazebrouck | ............... | A61F 2/389 623/20.32 |
| 2009/0084491 A1* | 4/2009 | Uthgenannt | ............... | A61F 2/389 156/153 |
| 2009/0088859 A1* | 4/2009 | Hazebrouck | ............... | A61F 2/389 623/20.14 |
| 2009/0125114 A1* | 5/2009 | May | ............... | A61B 17/1764 623/20.14 |
| 2009/0204222 A1* | 8/2009 | Burstein | ............... | A61B 17/157 623/20.34 |
| 2009/0265011 A1* | 10/2009 | Mandell | ............... | A61B 17/155 623/20.15 |
| 2009/0265013 A1* | 10/2009 | Mandell | ............... | A61F 2/38 623/20.21 |
| 2010/0063594 A1* | 3/2010 | Hazebrouck | ............... | A61F 2/38 623/20.29 |
| 2010/0100190 A1* | 4/2010 | May | ............... | A61F 2/38 623/20.14 |
| 2011/0029090 A1* | 2/2011 | Zannis | ............... | A61F 2/389 623/20.28 |
| 2011/0035017 A1* | 2/2011 | Deffenbaugh | ............... | A61F 2/389 623/20.14 |
| 2011/0035018 A1* | 2/2011 | Deffenbaugh | ............... | A61F 2/389 623/20.28 |
| 2011/0046735 A1* | 2/2011 | Metzger | ............... | A61B 19/50 623/14.12 |
| 2011/0178605 A1* | 7/2011 | Auger | ............... | A61F 2/3868 623/20.15 |
| 2011/0202139 A1* | 8/2011 | Metzger | ............... | A61F 2/3868 623/20.28 |
| 2012/0022658 A1* | 1/2012 | Wentorf | ............... | A61F 2/389 623/20.28 |
| 2012/0022660 A1* | 1/2012 | Wentorf | ............... | A61F 2/389 623/20.32 |
| 2012/0029649 A1* | 2/2012 | Collazo | ............... | A61F 2/3886 623/20.28 |
| 2012/0303122 A1* | 11/2012 | Servidio | ............... | A61F 2/389 623/14.12 |
| 2013/0006374 A1* | 1/2013 | Le Couedic | ............... | A61F 2/3868 623/20.28 |
| 2013/0079885 A1* | 3/2013 | Meier | ............... | A61F 2/38 623/20.21 |
| 2013/0184829 A1* | 7/2013 | Wyss | ............... | A61F 2/38 623/20.28 |
| 2014/0107794 A1* | 4/2014 | Deffenbaugh | ............... | A61F 2/389 623/20.28 |
| 2015/0202048 A1* | 7/2015 | Roisin | ............... | A61F 2/389 623/20.32 |

FOREIGN PATENT DOCUMENTS

FR   2 719 213 A1   11/1995
WO   01/41680 A1   6/2001

* cited by examiner

PROSTHETIC TIBIAL BASE, AND PROSTHETIC TIBIAL INSERT INTENDED TO BE IMMOBILIZED ON SUCH A PROSTHETIC TIBIAL BASE

The present invention relates to a prosthetic tibial base intended to immobilize a prosthetic tibial insert. Moreover, the present invention relates to a prosthetic tibial insert intended to be immobilized on such a prosthetic tibial base.

The present invention may also be applied in particular in the field of knee prostheses, particularly for the replacement of the proximal part of the tibia.

In the background art, there exists a tibial base comprising, on the one hand, means for attaching onto a resected part of the tibia of a patient and, on the other hand, a platen of which the lateral and medial edges have pins to assemble a tibial insert thereto. The tibial base is usually in a metal alloy and the tibial insert is usually in a synthetic polymer material, such as polyethylene.

However, it has been noted that attaching a tibial insert onto such a tibial base generated a sort of clearance, particularly along an anteroposterior direction, thus inducing friction of the tibial insert on the tibial base in service. The wear caused by this friction risks generating small debris of tibial insert, which may cause osteolysis.

One purpose of the present invention is in particular to resolve, wholly or partially, the aforementioned issues.

To this purpose, the object of the invention is a prosthetic tibial base, intended to immobilize a prosthetic tibial insert configured to be articulated with femoral condyles, the prosthetic tibial base comprising i) osseous attachment means for attaching the prosthetic tibial base onto a resected part of the tibia of a patient, and ii) a platen comprising at least:
  a plate configured to receive an inferior complementary face of the prosthetic tibial insert, the plate being delimited by a posterior edge, by an anterior edge opposite to the posterior edge, by a medial edge and by a lateral edge opposite to the medial edge;
  a posterior pin protruding above the plate, the posterior pin being disposed, along a medio-lateral direction, on a median region of the posterior edge, the posterior pin having a posterior flat section oriented towards the anterior edge, preferably parallel to the frontal plane;
  an anterior pin protruding above the plate, the anterior pin being disposed, along a medio-lateral direction, on a median region of the anterior edge, the anterior pin having an anterior flat section oriented towards the posterior edge, preferably parallel to the frontal plane;
  two posterior lugs protruding above the plate, the two posterior lugs being disposed on the posterior edge and respectively on each side of the posterior pin;
  two anterior lugs protruding above the plate, the two anterior lugs being disposed on the anterior edge and respectively on each side of the anterior pin;
  the posterior flat section and the anterior flat section are arranged in such a manner that the prosthetic tibial insert may bear simultaneously against the posterior flat section and against the anterior flat section;
  each posterior lug comprises a respective retaining extension for retaining the prosthetic tibial insert on the prosthetic tibial base, each retaining extension being configured for allowing the insertion, under the retaining extension and along an anteroposterior direction, of a complementary retaining tab belonging to the prosthetic tibial insert;
  each anterior lug comprises means for elastic snap-fitting the prosthetic tibial insert onto the prosthetic tibial base.

Thus, such a prosthetic tibial base allows attaching a prosthetic tibial insert without clearance or with insignificant clearance, particularly along the anteroposterior direction, thus preventing any clearance in the prosthesis and hence the premature wear of the prosthetic tibial insert.

According to an embodiment of the invention, the distance separating the posterior flat section from the anterior flat section, measured along an anteroposterior direction, is determined in such a manner as to press-fit the prosthetic tibial insert.

Thus, such press-fitting allows to firmly attach the prosthetic tibial insert onto the prosthetic tibial base.

According to an embodiment of the invention, the prosthetic tibial base further comprises:
  a medial lug protruding above the plateau, the medial lug being disposed on the medial edge, the medial lug comprising a retaining wing for retaining the prosthetic tibial insert on the prosthetic tibial base, the retaining wing being configured to allow the insertion, under the retaining wing and along a medio-lateral direction of a complementary retaining tenon belonging to the prosthetic tibial insert; and
  a lateral lug protruding above the plate, the lateral lug being disposed on the lateral edge, the lateral lug including a retaining wing for retaining the prosthetic tibial insert on the prosthetic tibial base, the retaining wing being configured to allow the insertion, under the retaining wing and along a medio-lateral direction of a complementary retaining tenon belonging to the prosthetic tibial insert.

According to an embodiment of the invention, the plate surface roughness has an arithmetic mean deviation lower than 0.1 µm, preferably lower than 0.05 µm.

In other words, the plate has a mirror finish.

Thus, such a smooth plate prevents the wear of the prosthetic tibial insert even when the attaching thereof has an insignificant clearance.

According to an embodiment of the invention, the plate has a planar plate surface, the plate surface preferably being perpendicular to the posterior pin, to the anterior pin, to the posterior lugs and to the anterior lugs.

Thus, such a plate surface allows distributing, evenly and on a large surface area, the forces transmitted between the prosthetic tibial insert and the prosthetic tibial base.

According to an embodiment of the invention, the posterior flat section and the anterior flat section are planar and parallel, the posterior flat section and the anterior flat section preferably being perpendicular to an anteroposterior direction.

Thus, such flat sections ensure the retaining of the prosthetic tibial insert on the prosthetic tibial base along the anteroposterior direction.

According to an embodiment of the invention, the posterior flat section and the anterior flat section are arranged in such a manner that the prosthetic tibial insert may be tightly inserted between the posterior flat section and the anterior flat section.

Thus, such a tight fit ensures an optimal retaining of the prosthetic tibial insert on the prosthetic tibial base.

According to an embodiment of the invention, each retaining extension has a transversal section in the shape of a dovetail.

Thus, such retaining extensions allow rapidly attaching the prosthetic tibial insert onto the prosthetic tibial base.

According to an embodiment of the invention, the plate is composed of a material selected from among the group consisting of cobalt-chrome alloy, type 316L or type M30NW stainless steel, and titanium alloy TA6V4Eli.

Thus, such a material allows achieving a prosthetic tibial base having a low friction coefficient.

According to an embodiment of the invention, a protective film covers at least the plate, the protective film being removable, in such a manner as to be removed during the surgical procedure prior to definitive impaction of the prosthetic tibial insert onto the prosthetic tibial base.

Thus, such a protective film allows protecting the base prior to the surgical procedure.

Furthermore, the object of the present invention is a prosthetic tibial insert, intended to be immobilized on a prosthetic tibial base, the prosthetic tibial insert having surfaces configured to be articulated with respective femoral condyles, the prosthetic tibial insert having an inferior portion comprising:

an inferior face configured to bear against a complementary plate of the io prosthetic tibial base, the inferior face being delimited by a posterior side, by an anterior side opposite the posterior side, by a medial side and by a lateral side opposite the medial side;

a posterior flat arranged on the posterior side, the posterior flat being disposed, along a medio-lateral direction, on a median region of the posterior side, the posterior flat being oriented towards the anterior side, preferably parallel to the frontal plane;

an anterior flat arranged on the anterior side, the anterior flat being disposed, along a medio-lateral direction, on a median region of the anterior side, the anterior flat being oriented towards the anterior side, preferably parallel to the frontal plane;

two posterior housings arranged on the posterior side, the two posterior housings on either side of the posterior flat;

two anterior members arranged on the anterior side, the two anterior members being disposed on the anterior side and respectively on either side of the anterior flat;

the posterior flat and the anterior flat are arranged in such a manner that the prosthetic tibial base may simultaneously bear against the posterior flat and against the anterior flat;

each posterior housing includes a retaining tab for retaining the prosthetic tibial insert on the prosthetic tibial base, each retaining tab being configured to be inserted, along an anteroposterior direction, under a complementary retaining extension belonging to the prosthetic tibial base;

each anterior member includes means for elastic snap-fitting the prosthetic tibial base onto the prosthetic tibial insert.

Thus, such a tibial insert may be attached on a prosthetic tibial base in accordance with the invention without clearance or with insignificant clearance, particularly along the anteroposterior direction, thus preventing any clearance in the prosthesis and hence the premature wear of the prosthetic tibial insert.

According to an embodiment of the invention, at least the inferior portion is composed of a material selected from the group consisting of ultra-high-molecular-weight polyethylene (UHMW-PE), polyurethane, and in which the inferior portion has a thickness higher than 1.5 mm.

Thus, such a material allows achieving a prosthetic tibial insert having a low friction coefficient.

The aforementioned embodiments and variants may be taken alone or according to any technically possible combination.

The present invention will be better understood and the advantages thereof will also become apparent in light of the following description, given only by way of non limiting example and made with reference to the accompanying drawings, in which.

Figure 1:
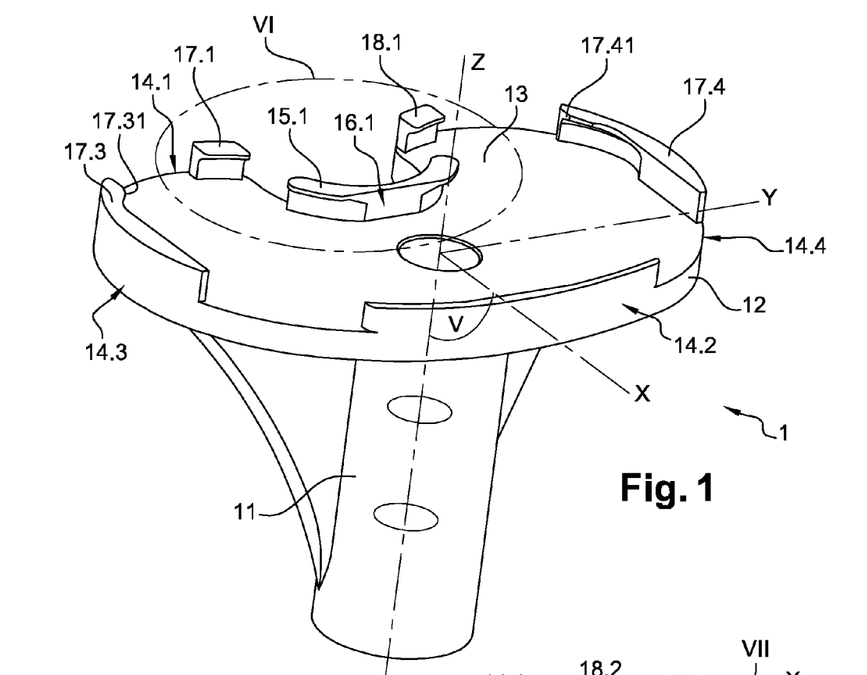
FIG. 1 is a perspective anterior view of a prosthetic tibial base in accordance with the invention.
Figure 2:
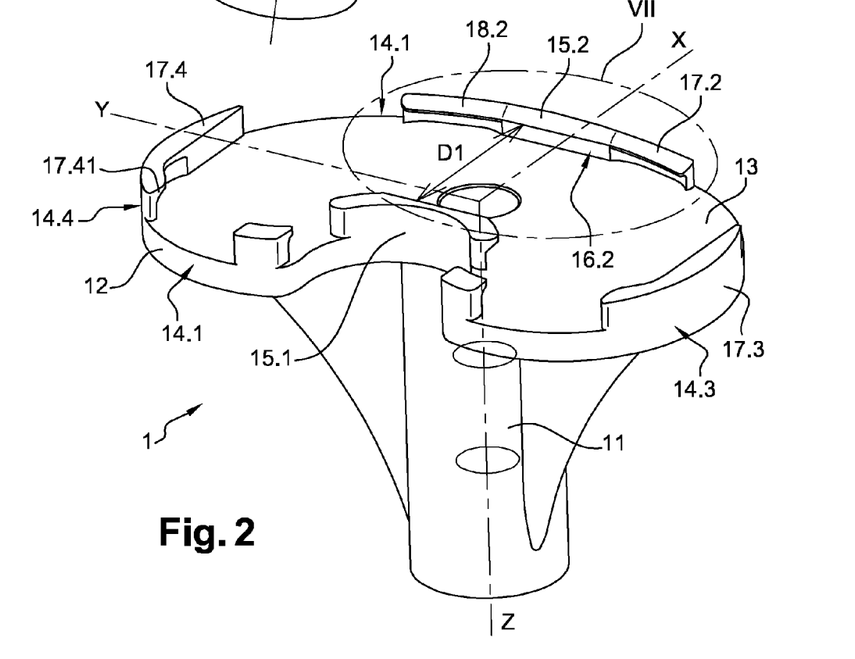
FIG. 2 is a perspective posterior view of the prosthetic tibial base of FIG. 1.
Figure 3:
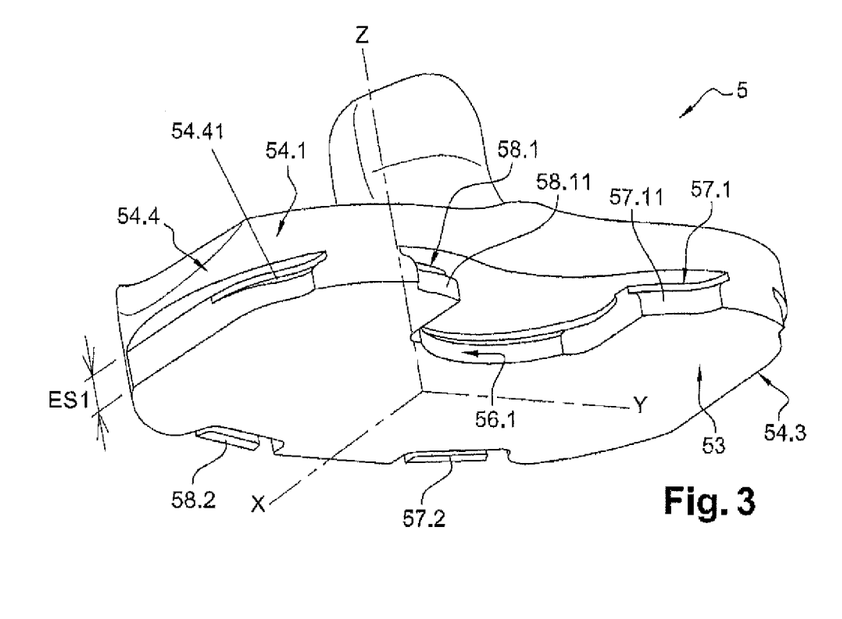
FIG. 3 is a perspective posterior view of a prosthetic tibial insert in accordance with the invention and intended to be immobilized on the prosthetic tibial base of FIGS. 1 and 2.
Figure 4:
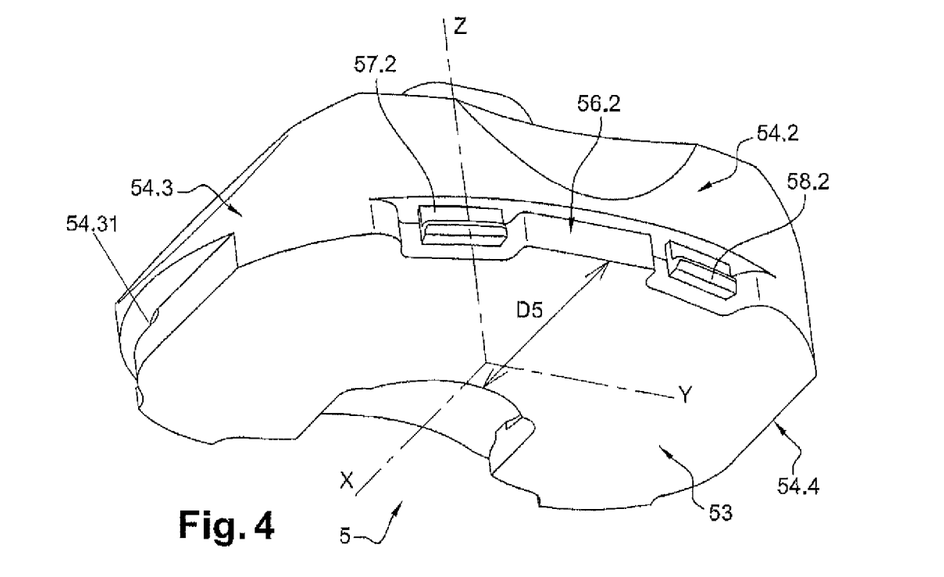
FIG. 4 is a perspective anterior view of the prosthetic tibial insert of FIG. 3.

FIGS. 1 and 2 illustrate a prosthetic tibial base 1, which is intended to immobilize a prosthetic tibial insert 5, illustrated on FIGS. 3 and 4. The prosthetic tibial insert 5 is configured to be articulated with non represented femoral condyles.

The prosthetic tibial base 1 comprises a platen 12 and osseous attachment means 11 for attaching the prosthetic tibial base 1 onto a resected part of the tibia of a patient.

The platen 12 comprises a plate 13 which is configured to receive a complementary inferior face 53 of the prosthetic tibial insert 5. The plate 13 is delimited by a posterior edge 14.1, by an anterior edge 14.2 opposite the posterior edge 14.1, by a medial edge 14.3 and by a lateral edge 14.4 opposite the medial edge 14.3.

The platen 12 also comprises a posterior pin 15.1 which protrudes above the plate 13, by around 2 mm. The posterior pin 15.1 is disposed, along a medio-lateral direction Y, on a median region of the posterior edge 14.1. The posterior pin 15.1 has a posterior flat section 16.1 oriented towards the anterior edge 14.2 and parallel to the frontal plane. The frontal plane separates the body in an anterior part and a posterior part. On FIGS. 1 and 2, the plane YZ represents the frontal plane. The direction Z is a sagittal direction.

The platen 12 further comprises an anterior pin 15.2 which protrudes above the plate 13, by around 2 mm. The anterior pin 15.2 is disposed, along a medio-lateral direction Y, on a median region of the anterior edge 14.2. The anterior pin 15.2 having an anterior flat section 16.2 oriented towards the posterior edge 14.1 and parallel to the frontal plane, hence the plane YZ.

Moreover, the platen 12 comprises two posterior lugs 17.1 and 18.1 which protrude above the plate 13, by around 2 mm. The two posterior lugs 17.1, 18.1 are disposed on the posterior edge 14.1 and respectively on each side of the posterior pin 15.1.

Similarly, the platen 12 comprises two anterior lugs 17.2 and 18.2 which protrude above the plate 13, by around 2 mm. The two anterior lugs 17.2, 18.2 are disposed on the anterior edge 14.2 and respectively on each side of the anterior pin 15.2.

The posterior flat section 16.1 and the anterior flat section 16.2 are arranged in such a manner that the prosthetic tibial insert 5 may bear simultaneously against the posterior flat section 16.1 and against the anterior flat section 16.2.

Each posterior lug 17.1 or 18.1 includes a respective retaining extension 17.11 and 18.11 in order to retain the prosthetic tibial insert 5 on the prosthetic tibial base 1. Each retaining extension 17.11 or 18.11 is configured to allow the insertion, under the retaining extension 17.11 or 18.11 and along an anteroposterior direction, of a complementary retaining tab 57.11 or 58.11 which belongs to the prosthetic tibial insert 5.

In the example of FIGS. 1 to 4, each retaining extension 17.11 or 18.11 has a transversal section in the shape of a dovetail, here an upturned "J".

Each anterior lug 17.2 or 18.2 includes means for elastically snap-fitting the prosthetic tibial insert 5 onto the prosthetic tibial base 1.

FIGS. 3 and 4 illustrate the prosthetic tibial insert 5, which is intended to be immobilized on the prosthetic tibial base 1. The prosthetic tibial insert 5 has surfaces configured to be articulated with respective non represented femoral condyles.

The prosthetic tibial insert 5 has an inferior portion 51 which comprises an inferior face 53 configured to bear against a complementary plate 13 of the prosthetic tibial base 1. The inferior face 53 is delimited by a posterior side 54.1, by an anterior side 54.2 opposite the posterior side 54.1, by a medial side 54.3 and by a lateral side 54.4 opposite the medial side 54.3.

The inferior portion 51 of the prosthetic tibial insert 5 also comprises:
  a posterior flat 56.1 which is arranged on the posterior side 54.1; the posterior flat 56.1 is disposed, along a medio-lateral direction Y, on a median region of the posterior side 54.1; the posterior flat 56.1 is oriented towards the posterior side 54.1 and parallel to the frontal plane, hence the plane YZ;
  an anterior flat 56.2 arranged on the anterior side 54.2; the anterior flat 54.2 is disposed, along a medio-lateral direction Y, on a median region of the anterior side 54.2; the anterior flat 56.2 is oriented towards the anterior side 54.2 and parallel to the frontal plane, hence the plane YZ; and
  two posterior housings 57.1 and 58.1 arranged on the posterior side 54.1, the posterior housings 57.1 and 58.1 on either side of the posterior flat 56.1.

Figure 5:
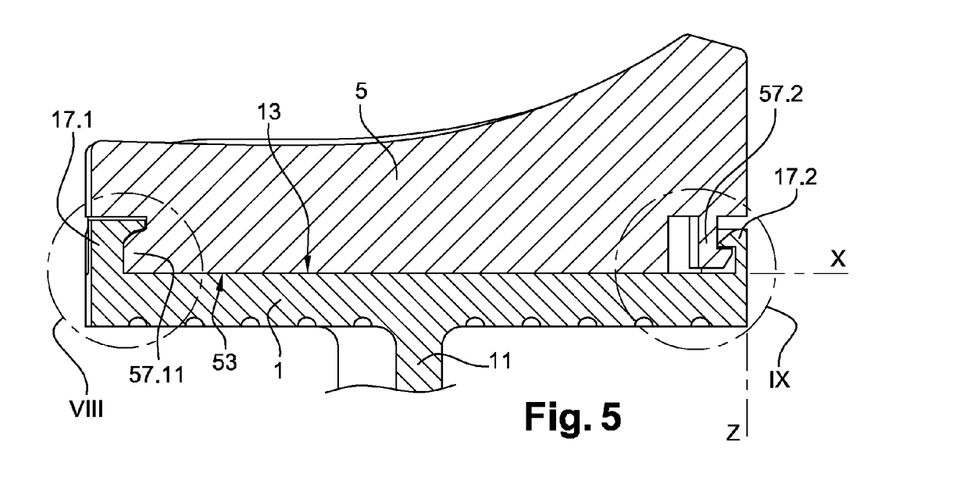
FIG. 5 is a sectional view along plane V on FIG. 1 and illustrating the prosthetic tibial insert of FIGS. 3 and 4 immobilized on the prosthetic tibial base of FIGS. 1 and 2.
Figure 6:
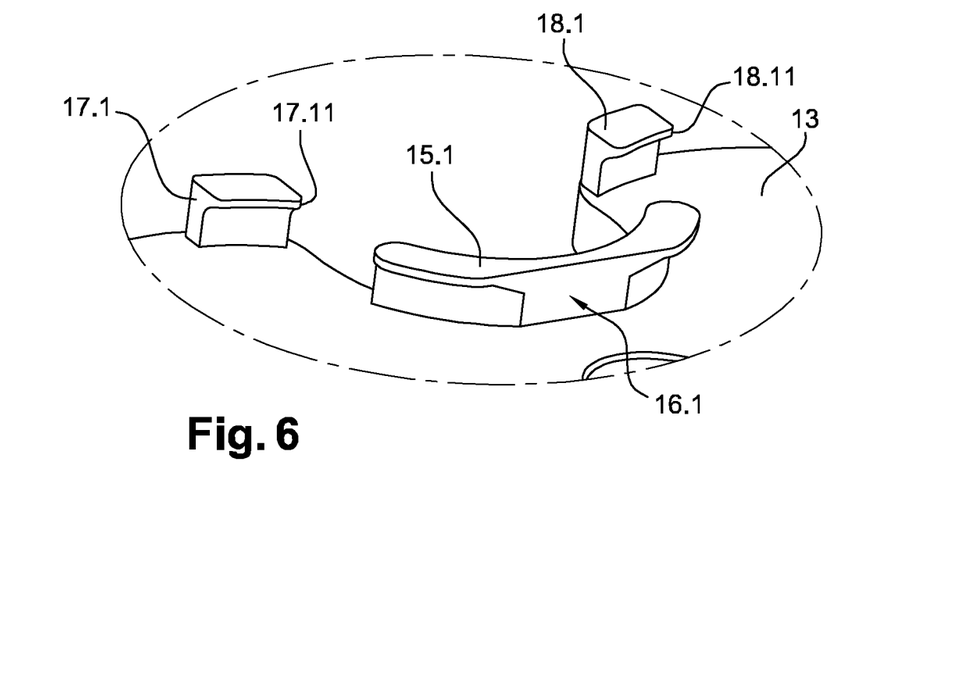
FIG. 6 is a larger scale view of the detail VI on FIG. 1.
Figure 7:
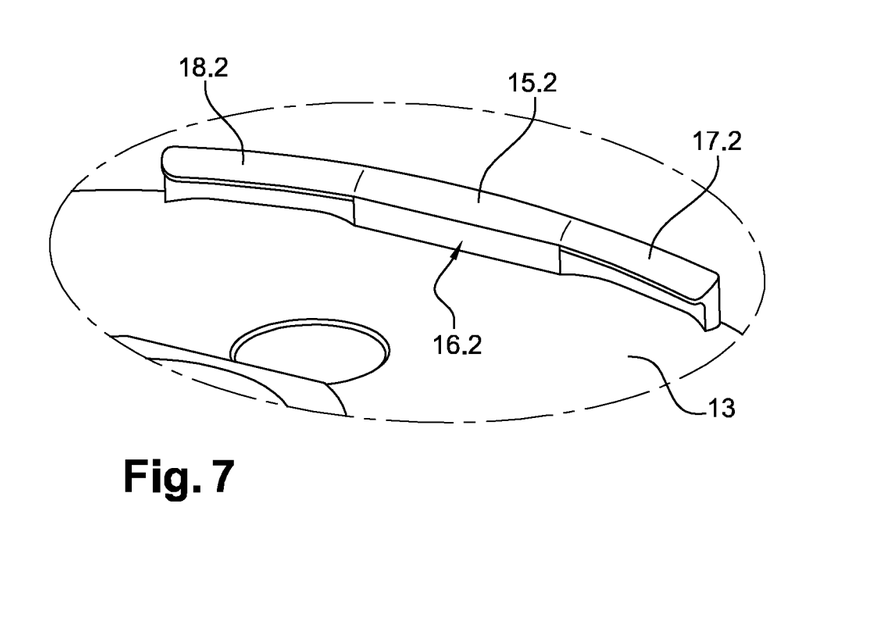
FIG. 7 is a larger scale view of the detail VII on FIG. 2.
Figures 8, 9:
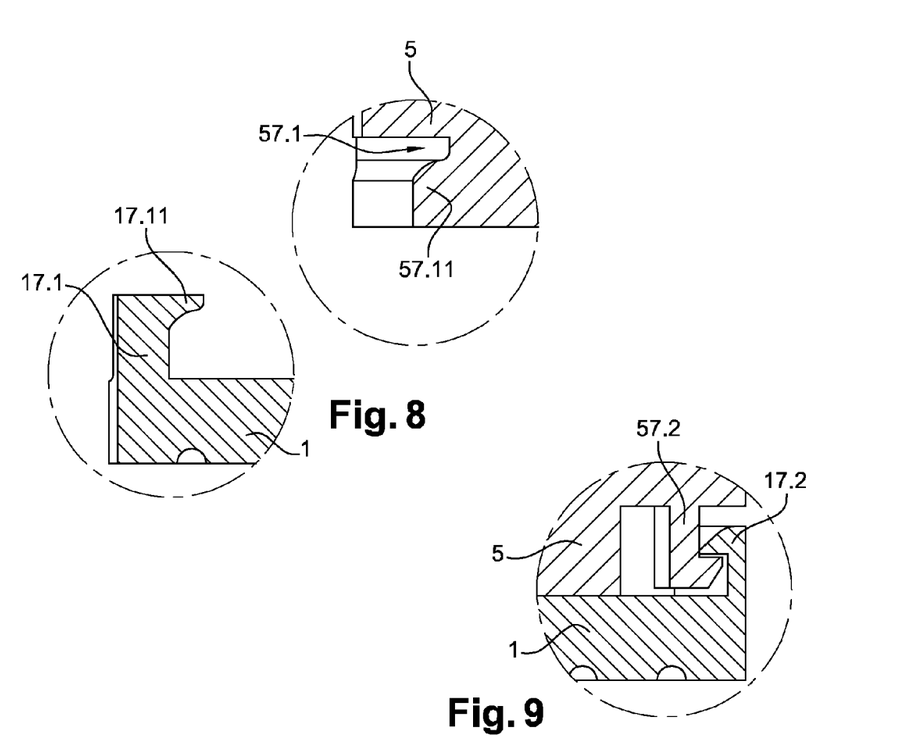
FIG. 8 is a larger scale exploded view of the detail VII on FIG. 5.
FIG. 9 is a larger scale view of the detail IX on FIG. 5.

When the prosthetic tibial insert 5 is immobilized on the prosthetic tibial base 1, the posterior 56.1 and anterior 56.2 flats respectively cooperate with the posterior 16.1 and anterior 16.2 flat sections. In order to obtain this cooperation, for a tibial insert of size 4 in a range of tibial inserts, the dimension between the surfaces 56.1 and 56.2 is 29.57 mm −0.1/−0.2 mm and the dimension between the flat sections 16.1 and 16.2 is 30.17 mm 0/−0.6 mm. The minimum clearance is hence 0 mm and the maximum clearance is 0.8 mm.

Moreover, the inferior portion 51 of the prosthetic tibial insert 5 comprises two anterior members 57.2 and 58.2 arranged on the anterior side 54.2. The two anterior members 57.2 and 58.2 are disposed on the anterior side 54.2 and respectively on either side of the anterior flat 56.2.

The posterior flat 56.1 and the anterior flat 56.2 are arranged in such a manner that the prosthetic tibial base 1 may simultaneously bear against the posterior flat 56.1 and against the anterior flat 56.2.

Each posterior housing 57.1 or 58.1 includes a retaining tab 57.11 or 58.11 in order to retain the prosthetic tibial insert 5 on the prosthetic tibial base 1. Each retaining tab 57.11 or 58.11 is configured to be inserted, along an anteroposterior direction X, under a complementary retaining extension 17.11 or 18.11 which belongs to the prosthetic tibial base 1.

Each anterior member 57.2 or 58.2 includes means for elastic snap-fitting the prosthetic tibial base 1 onto the prosthetic tibial insert 5.

Furthermore, the distance D1 between a posterior flat section 16.1 and the anterior flat section 16.2, measured along an anteroposterior direction X, is determined in such a manner as to achieve a press-fitting of the prosthetic tibial insert 5. In a complementary manner, the distance D5 between the posterior flat 56.1, measured along an anteroposterior direction X, is determined in such a manner as to achieve a press-fitting of the prosthetic tibial insert 5. In the example of FIGS. 1 to 4, the distance D1 measures 30.17 mm 0/−0.6 mm and the distance D5 measures 29.57 mm −0.1/−0.2 mm.

The prosthetic tibial base 1 further comprises:
  a medial lug 17.3 which protrudes above the plate 13, by around 2 mm; the medial lug 17.3 is disposed on the medial edge 14.3; the medial lug 17.3 includes a medial retaining wing 17.31 for retaining the prosthetic tibial insert 5 on the prosthetic tibial base 1; the medial retaining wing 17.31 is configured to allow the insertion, under the retaining wing and along a medio-lateral direction Y of a complementary retaining tenon which belongs to the prosthetic tibial insert 5; and
  a lateral lug 17.4 which protrudes above the plate 13; the lateral lug 17.4 is disposed on the lateral edge 14.4; the lateral lug 17.4 includes a lateral retaining wing 17.41 in order to retain the prosthetic tibial insert 5 on the prosthetic tibial base 1; the lateral retaining wing 17.41 is configured to allow the insertion, under the retaining wing 17.41 and along a medio-lateral direction Y of a complementary retaining tenon which belongs to the prosthetic tibial insert 5.

Furthermore, the surface roughness of the plate 13 has an arithmetic mean deviation (Ra) which is around 0.05 µm. The plate 13 hence has a mirror finish surface roughness.

Moreover, the plate 13 has a plate surface which is planar and which is here perpendicular to the posterior pin 15.1, to the anterior pin 15.2, to the posterior lugs 17.1 and 18.1 and to the anterior lugs 17.2 and 18.2.

The posterior flat section 16.1 and the anterior flat section 16.2 are planar and parallel and are here perpendicular to the anteroposterior direction X. The posterior flat section 16.1 and the anterior flat section 16.2 are arranged in such a manner that the prosthetic tibial insert 5 may be inserted in a tight fit between the posterior flat section 16.1 and the anterior flat section 16.2.

The platen 12 of the prosthetic tibial base 1 is here composed of a cobalt-chrome alloy. The inferior portion 51 of the prosthetic tibial insert 5 is here composed of an ultra-high-molecular-weight polyethylene (UHMW-PE), The inferior portion 51 has here a thickness E51 of 3.5 mm +/−0.05 mm.

It may be provided a protective film covering the plate 13. This protective film is removable in such a manner as to be removed during the surgical procedure prior to definitive impaction of the prosthetic tibial insert 5 io onto the prosthetic tibial base 1.

The invention claimed is:

1. A prosthetic tibial base, intended to immobilize a prosthetic tibial insert configured to be articulated with femoral condyles, the prosthetic tibial base comprising:
  an osseous attachment part for attaching the prosthetic tibial base onto a resected part of the tibia of a patient:
  a platen that comprises:
    a plate configured to receive an inferior complementary face of the prosthetic tibial insert, the plate being delimited by a posterior edge, by an anterior edge opposite the posterior edge, by a medial edge and by a lateral edge opposite the medial edge;

a posterior pin protruding above the plate, the posterior pin being disposed, along a medio-lateral direction, on a median region of the posterior edge, the posterior pin having a posterior flat section oriented towards the anterior edge;

an anterior pin protruding above the plate, the anterior pin being disposed, along a medio-lateral direction, on a median region of the anterior edge, the anterior pin having an anterior flat section oriented towards the posterior edge;

two posterior lugs protruding above the plate, the two posterior lugs being disposed on the posterior edge and respectively on each side of the posterior pin;

two anterior lugs protruding above the plate, the two anterior lugs being disposed on the anterior edge and respectively on each side of the anterior pin; the posterior flat section and the anterior flat section are arranged in such a manner that the prosthetic tibial insert may bear simultaneously against the posterior flat section and against the anterior flat section wherein:

each posterior lug includes a respective retaining extension for retaining the prosthetic tibial insert on the prosthetic tibial base, each retaining extension being configured to allow the insertion, under the retaining extension and along an anteroposterior direction, of a complementary retaining tab belonging to the prosthetic tibial insert;

each anterior lug includes a resilient part for elastic snap-fitting the prosthetic tibial insert onto the prosthetic tibial base;

a medial lug protruding above the plate, the medial lug being disposed on the medial edge, the medial lug including a medial retaining wing for retaining the prosthetic tibial insert on the prosthetic tibial base, the medial retaining wing being configured to allow the insertion, under the medial retaining wing and along a medio-lateral direction of a complementary medial retaining tenon belonging to the prosthetic tibial insert; and a lateral lug protruding above the plate, the lateral lug being disposed on the lateral edge, the lateral lug including a lateral retaining wing for retaining the prosthetic tibial insert on the prosthetic tibial base, the lateral retaining wing being configured to allow the insertion, under the lateral retaining wing and along a medio-lateral direction of a complementary lateral retaining tenon belonging to the prosthetic tibial insert.

2. The prosthetic tibial base according to claim 1, wherein a distance separating the posterior flat section from the anterior flat section, measured along an anteroposterior direction, is determined in such a manner as to press-fit the prosthetic tibial insert.

3. The prosthetic tibial base according to claim 1, wherein the surface roughness of the plate has an arithmetic mean deviation lower than 0.1 μm.

4. The prosthetic tibial base according to claim 1, wherein the plate has a planar plate surface.

5. The prosthetic tibial base according to claim 4, wherein the plate surface is perpendicular to the posterior pin, to the anterior pin, to the posterior lugs and to the anterior lugs.

6. The prosthetic tibial base according to claim 5, wherein the posterior flat section and the anterior flat section are arranged in such a manner that the prosthetic tibial insert may be tightly inserted between the posterior flat section and the anterior flat section.

7. The prosthetic tibial base according to claim 1, wherein each retaining extension has a transversal section in the shape of a dovetail.

8. The prosthetic tibial base according to claim 1, wherein the platen is composed of a material selected from among the group consisting of cobalt-chrome alloy, type 316L or type M30NW stainless steel, and titanium alloy TA6V4E1i.

9. The prosthetic tibial base according to claim 1, wherein a protective film covers at least the plate, the protective film being removable, in such a manner as to be removed during the surgical procedure prior to definitive impaction of the prosthetic tibial insert onto the prosthetic tibial base.

10. The prosthetic tibial base according to claim 1, wherein the posterior flat section is oriented parallel to the frontal plane.

11. The prosthetic tibial base according to claim 1, wherein the anterior flat section is oriented parallel to the frontal plane.

12. The prosthetic tibial base according to claim 1, wherein the posterior flat section and the anterior flat section are perpendicular to an anteroposterior direction.

13. A prosthetic tibial base, intended to immobilize a prosthetic tibial insert configured to be articulated with femoral condyles, the prosthetic tibial base comprising:

osseous attachment part for attaching the prosthetic tibial base onto a resected part of the tibia of a patient; and a platen comprising:

a plate configured to receive an inferior complementary face of the prosthetic tibial insert, the plate being delimited by a posterior edge, by an anterior edge opposite the posterior edge, by a medial edge and by a lateral edge opposite the medial edge;

a posterior pin protruding above the plate, the posterior pin being disposed, along a medio-lateral direction, on a median region of the posterior edge, the posterior pin having a posterior flat section oriented towards the anterior edge;

an anterior pin protruding above the plate, the anterior pin being disposed, along a medio-lateral direction, on a median region of the anterior edge, the anterior pin having an anterior flat section oriented towards the posterior edge;

two posterior lugs protruding above the plate, the two posterior lugs being disposed on the posterior edge and respectively on each side of the posterior pin;

two anterior lugs protruding above the plate, the two anterior lugs being disposed on the anterior edge and respectively on each side of the anterior pin;

the posterior flat section and the anterior flat section are arranged in such a manner that the prosthetic tibial insert may bear simultaneously against the posterior flat section and against the anterior flat section;

each posterior lug includes a respective retaining extension for retaining the prosthetic tibial insert on the prosthetic tibial base, each retaining extension being configured to allow the insertion, under the retaining extension and along an anteroposterior direction, of a complementary retaining tab belonging to the prosthetic tibial insert;

each anterior lug includes a resilient part for elastic snap-fitting the prosthetic tibial insert onto the prosthetic tibial base, wherein:

the posterior flat section and the anterior flat section are planar and parallel, the posterior flat section and the anterior flat section are facing each other, and at least one of the anterior lugs has a posterior edge extending beyond the anterior flat.

14. A prosthetic tibial insert, intended to be immobilized on a prosthetic tibial base, the prosthetic tibial insert comprising:

surfaces configured to be articulated with respective femoral condyles, and an inferior portion comprising:

an inferior face configured to bear against a complementary plate of the prosthetic tibial base, the inferior face being delimited by a posterior side, by an anterior side opposite the posterior side, by a medial side and by a lateral side opposite the medial side;

a posterior flat arranged on the posterior side, the posterior flat being disposed, along a medio-lateral direction, on a median region of the posterior side, the posterior flat being oriented towards the posterior side;

an anterior flat arranged on the anterior side, the anterior flat being disposed, along a medio-lateral direction, on a median region of the anterior side, the anterior flat being oriented towards the anterior side;

two posterior housings arranged on the posterior side, the two posterior housings being located respectively on either side of the posterior flat;

two anterior members arranged on the anterior side, the two anterior members being located on the anterior side and respectively on either side of the anterior flat; the posterior flat and the anterior flat are arranged in such a manner that the prosthetic tibial base may simultaneously bear against the posterior flat and against the anterior flat, wherein:

each posterior housing includes a retaining tab for retaining the prosthetic tibial insert on the prosthetic tibial base, each retaining tab being configured to be inserted, along an anteroposterior direction, under a complementary retaining extension belonging to the prosthetic tibial base;

each anterior member includes a resilient part for elastic snap-fitting the prosthetic tibial base onto the prosthetic tibial insert, the prosthetic tibial base further comprises:

a medial lug protruding above the plate, the medial lug being disposed on the medial edge, the medial lug including a medial retaining wing for retaining the prosthetic tibial insert on the prosthetic tibial base, the medial retaining wing being configured to allow the insertion, under the medial retaining wing and along a medio-lateral direction of a complementary medial retaining tenon belonging to the prosthetic tibial insert; and a lateral lug protruding above the plate, the lateral lug being disposed on the lateral edge, the lateral lug including a lateral retaining wing for retaining the prosthetic tibial insert on the prosthetic tibial base, the lateral retaining wing being configured to allow the insertion, under the lateral retaining wing and along a medio-lateral direction of a complementary lateral retaining tenon belonging to the prosthetic tibial insert.

15. The prosthetic tibial insert according to claim 14, wherein at least the inferior portion is composed of a material selected from the group consisting of ultra-high-molecular-weight polyethylene (UHMW-PE), polyurethane, and wherein the inferior portion has a thickness higher than 1.5 mm.

16. A prosthetic tibial insert, intended to be immobilized on a prosthetic tibial base, the prosthetic tibial insert having surfaces configured to be articulated with respective femoral condyles, the prosthetic tibial insert having an inferior portion comprising:

an inferior face configured to bear against a complementary plate of the prosthetic tibial base, the inferior face being delimited by a posterior side, by an anterior side opposite the posterior side, by a medial side and by a lateral side opposite the medial side;

a posterior flat arranged on the posterior side, the posterior flat being disposed, along a medio-lateral direction, on a median region of the posterior side, the posterior flat being oriented towards the posterior side;

an anterior flat arranged on the anterior side, the anterior flat being disposed, along a medio-lateral direction, on a median region of the anterior side, the anterior flat being oriented towards the anterior side;

two posterior housings arranged on the posterior side, the two posterior housings being located respectively on either side of the posterior flat;

two anterior members arranged on the anterior side, the two anterior members being located on the anterior side and respectively on either side of the anterior flat; the posterior flat and the anterior flat are arranged in such a manner that the prosthetic tibial base may simultaneously bear against the posterior flat and against the anterior flat, wherein:

each posterior housing includes a retaining tab for retaining the prosthetic tibial insert on the prosthetic tibial base, each retaining tab being configured to be inserted, along an anteroposterior direction, under a complementary retaining extension belonging to the prosthetic tibial base;

each anterior member includes a resilient part for elastic snap-fitting the prosthetic tibial base onto the prosthetic tibial insert, the posterior flat and the anterior flat are parallel to the frontal plane, the posterior flat and the anterior flat are facing each other, and at least one of the anterior members has a posterior border extending beyond the anterior flat along the anteroposterior direction and toward the posterior flat.

* * * * *